United States Patent [19]

Tsuchihashi et al.

[11] 4,278,802

[45] Jul. 14, 1981

[54] NOVEL α-THIO-ALKANOIC ACID DERIVATIVES

[75] Inventors: Genichi Tsuchihashi, Tama; Katsuyuki Ogura; Shuichi Mitamura, both of Sagamihara, all of Japan

[73] Assignee: Sagami Chemical Research Center, Japan

[21] Appl. No.: 156,349

[22] Filed: Jun. 4, 1980

Related U.S. Application Data

[60] Division of Ser. No. 20,231, Mar. 13, 1979, which is a continuation of Ser. No. 843,343, Oct. 18, 1977, abandoned.

[30] Foreign Application Priority Data

Oct. 18, 1976 [JP] Japan ............................. 51-123903
Oct. 18, 1976 [JP] Japan ............................. 51-123904
Dec. 27, 1976 [JP] Japan ............................. 51-156358
Dec. 27, 1976 [JP] Japan ............................. 51-156360

[51] Int. Cl.$^3$ .................... C07D 333/48; A61K 31/38
[52] U.S. Cl. ........................................ 549/72; 424/275
[58] Field of Search ........................................ 549/72

[56] References Cited

U.S. PATENT DOCUMENTS 4,064,132  12/1977  Janssen et al. ..................... 549/72
4,159,986   7/1979  Clemence et al. .................. 549/72

Primary Examiner—Alan Siegel
Attorney, Agent, or Firm—Wenderoth, Lind & Ponack

[57] ABSTRACT

Novel α-thio-alkanoic acid derivatives and a process for their preparation. These novel compounds can be easily converted to useful medicines.

1 Claim, No Drawings

NOVEL α-THIO-ALKANOIC ACID DERIVATIVES

This is a Division, of application Ser. No. 20,231, filed Mar. 13, 1979, which in turn is a continuation of Ser. No. 843,343 filed Oct. 18, 1977, now abandoned.

This invention relates to novel α-thio-alkanoic acid derivatives of the formula

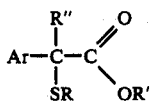

(II)

wherein Ar represents a substituted phenyl group, a substituted naphthyl group, or an unsubstituted or substituted heterocyclic aromatic group; R" represents a lower alkyl group containing 1 to 4 carbon atoms; R represents a lower alkyl group containing 1 to 4 carbon atoms or an aryl group; and R' represents a hydrogen atom or a lower alkyl group containing 1 to 4 carbon atoms. It also relates to a process for preparing said novel compounds, and to the use of these compounds.

These derivatives are characterized by the fact that a specified aromatic group, alkyl group and alkylthio or arylthio group are bonded to the carbon atom at the position adjacent to the carboxyl or alkoxycarbonyl group. These compounds, as will be described hereinbelow, are novel useful compounds which can be easily converted into useful medicines.

In formula (II), the substituent at the substituted phenyl group represented by Ar may be a wide range of organic groups. Examples of the substituent are lower alkyl groups, halogen atoms, aryloxy groups, substituted or unsubstituted amino groups, acyl groups, and acetal-protected acyl groups.

Specific examples of the substituted naphthyl group represented by Ar include naphthyl groups substituted with alkoxy.

Examples of the substituted or unsubstituted heterocyclic aromatic group represented by Ar include a thienyl group, acyl-substituted thienyl groups, and thienyl groups substituted with acetal-protected acyl.

According to the present invention, the novel compounds of formula (II) can be easily produced by reacting α-thio-acetic acid derivatives of the formula

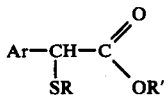

(I)

wherein Ar, R and R' are as defined above, with an alkylating agent containing a lower alkyl group R" in the presence of bases. Compounds of formula (I) in which R' is alkyl, i.e. the esters, can, if desired, be converted by hydrolysis to compounds of formula (II) in which R' is hydrogen, i.e. the free acids.

The compounds of formula (II) can be easily prepared by the process of this invention as shown above, but such a process has never been known before.

No report has been made in the literature about the synthesis of the compounds of formula (II). The only report which has some bearing on this subject is about the synthesis of ethyl α-phenylthio-α-phenylpropionate, an analogous compound, which is given in J. Amer. Chem. Soc., 74, 1034 (1952). This synthetic process comprises reacting acetophenone with sodium cyanide to synthesize atrolactic acid (Organic Syntheses Coll. Vol. IV, 58); esterifying this compound to form ethyl atrolactate, reacting it with phosphorus pentachloride to form ethyl α-chloro-α-phenylpropionate; and reacting ethyl α-chloro-α-phenylpropionate with thiophenol in the presence of sodium ethoxide to give the desired ethyl α-phenylthio-α-phenylpropionate. However, this conventional method has the defect that the synthesis of atrolactic acid in the first step requires the use of highly toxic sodium cyanide, induces the formation of highly toxic hydrogen cyanide during the reaction operation, and gives the product only in low yields (29 to 30%). Hence, it cannot find commercial application. In contrast, the present invention provides a quite new and commercially advantageous process for producing the compounds of formula (II).

The starting compounds of formula (I) used in this invention can be synthesized safely and in high yields without the use of a toxic substance such as sodium cyanide. No difficulty is encountered either in converting the compounds of formula (I) into the compounds of formula (II).

The α-alkylthio-acetic acid derivatives of the type of formula (I) used as a starting material for the production of the compounds of formula (II) and a process for their production are disclosed in U.S. Patent Application Ser. No. 773,114 filed Feb. 28, 1977. Briefly stated, the process comprises reacting α-chloroketene mercaptals with alcohols in the presence of acid catalysts. The α-chloroketenes are compounds which can be easily derived from the corresponding aromatic aldehydes that are easily available commercially and can be synthesized with simplicity.

Preferred embodiments of the process of this invention for producing the compounds of formula (II) are described below.

Preferred alkylating agents are alkyl halides such as alkyl iodides, bromides or chlorides or active alkyl esters such as dialkyl sulfates, trialkyl phosphates, and alkyl sulfonates.

The bases in the presence of which the alkylation reaction is performed are strong bases capable of generating an anion on the carbon atom bonded to the group Ar in the compound of formula (I). Specific examples include alkali metal hydrides such as sodium hydride and potassium hydride; organolithium compounds such as methyllithium, butyllithium, phenyllithium, lithium diethylamide, or lithium diisopropylamide; and sodium amide and naphthalene-sodium.

It is sufficient that the alkylation agents and bases are used in substantially stoichiometrical amounts based on the starting compound. When R' in the compound of formula (I) is an alkyl, the stoichiometrical amount of the base is one equivalent, whereas when R' is hydrogen, the stoichiometrical amount of the base is two equivalents.

The reaction is carried out preferably in a solvent. Preferred solvents are aprotic solvents such as dimethylformamide (DMF), dimethyl sulfoxide (DMSO), tetrahydrofuran (THF), and 1,2-dimethoxyethane.

The reaction proceeds smoothly at −40° to 100° C., preferably −20° to 70° C.

Conversion of the compounds of formula (II) in the form of esters (R'=alkyl) to the corresponding compounds in acid form (R'=H) is normally effected by alkaline hydrolysis. Usable alkaline substances are hydroxides or carbonates of alkali metals, such as sodium hydroxide, potassium hydroxide, sodium carbonate and potassium carbonate. Preferably, the amount of the alkaline substance is at least 1 mole per mole of the starting material. The hydrolysis is conveniently performed in water, an alcohol, an alcohol-water mixture, a water-1,2-dimethoxyethane mixture or a water-THF mixture.

The compound of formula (II) can be separated and recovered from the reaction mixture in a customary manner, for example by distillation, extraction or chromatography.

The novel compounds of formula (II) can be easily converted into useful medicinal substances. Typical examples of these medicines are Ibuprofen [α-(p-isobutylphenyl)propionic acid], Fenoprofen [α-(m-phenoxyphenyl)propionic acid], Indoprofen (α-[p-(1-oxo-2-isoindolinyl)phenyl]propionic acid), Ketoprofen [α-(m-benzoylphenyl)propionic acid], Naproxen [α-(6-methoxy-2-naphthyl)propionic acid], Suprofen (α-[4-(2-thienylcarbonyl)phenyl]propionic acid), Thioprofenic acid [α-(5-benzoyl-2-thienyl)propionic acid]. These medicines are widely used because of their excellent anti-inflammatory, analgesic and antipyretic actions. Conventional methods for producing these pharmaceuticals, however, are complicated and industrially disadvantageous. Since this fact has some bearing in demonstrating the advantages of the present invention, methods for producing these known pharmaceutical substances are described below at some length.

Typical methods for producing Ibuprofen, which have been used heretofore, are as follows.

(A) The method which comprises reacting a p-isobutylphenylacetic acid ester with a dialkyl carbonate in the presence of a base to produce the corresponding malonic acid ester, methylating the malonic acid ester with methyl iodide, hydrolyzing the methylated product, and subsequently pyrolyzing the hydrolyzate to obtain the desired propionic acid (British Pat. No. 971,700/64; and Japanese Patent Publication No. 7491/65).

(B) The method which comprises converting p-isobutylacetophenone to the corresponding hydantoin by the action of potassium cyanide and ammonium carbonate, hydrolyzing the hydantoin to form an α-amino acid, alkylating it to form a dialkylamino compound, and then reducing it to form α-(p-isobutylphenyl)propionic acid (Japanese Patent Publication No. 18105/72).

(C) The method which comprises subjecting p-isobutylacetophenone and a chloroacetic acid ester of the Darzen reaction to form the corresponding epoxycarboxylic acid ester, hydrolyzing the product, decarboxylating the hydrolyzate to form α-(p-isobutylphenyl)propionaldehyde, and oxidizing it to form the desired propionic acid (Japanese Patent Publication No. 24550/72).

All of these conventional methods start from p-isobutylacetophenone. p-Isobutylacetophenone can be prepared by a Friedel-Crafts reaction of isobutylbenzene with acetyl chloride. Since aluminum chloride is used in this reaction in an amount of more than 1 mole per mole of the starting compounds, a large quantity of aluminum hydroxide formed by a usual work-up in mass production causes serious troubles in isolating the desired product or in disposing of the waste matter.

The following two methods have heretofore been known for the production of Fenoprofen.

(1) The method which comprises reducing m-phenoxyacetophenone with sodium borohydride to form m-phenoxy-α-phenethyl alcohol, reacting it with phosphorus tribromide to form m-phenoxy-α-phenetyl bromide, reacting it with sodium cyanide in dimethyl sulfoxide under heating, and hydrolyzing the reaction product using sodium hydroxide to give the desired α-(m-phenoxyphenyl)propionic acid (see U.S. Pat. No. 3,600,437).

(2) The method which comprises brominating m-methyldiphenyl ether with N-bromosuccinimide to form m-(bromomethyl)diphenyl ether, reacting the ether with sodium cyanide in dimethyl sulfoxide to form m-(cyanoethyl)diphenyl ether, hydrolyzing and esterifying the product to form ethyl α-(m-phenoxyphenyl)acetate, reacting the ester with diethyl carbonate in the presence of metallic sodium to form diethyl 2-(m-phenoxyphenyl)malonate, methylation with methyliodide to give diethyl 2-methyl-2-(m-phenoxyphenyl)malonate, hydrolyzing the malonate to form 2-methyl-2-(m-phenoxyphenyl)malonic acid, and decarboxylating it under heating to produce α-(m-phenoxyphenyl)propionic acid (Japanese Patent Publication No. 45586/76).

In method (1), m-phenoxyacetophenone is used as a starting material. This compound is obtained by reacting m-hydroxyacetophenone, which is expensive and difficult to obtain, with bromobenzene in the presence of copper. The intermediate product, m-phenoxy-α-phenetyl bromide, is an unstable compound, and any method which goes through this compound is unsuitable for mass production. Furthermore, the use of highly toxic sodium cyanide cannot be avoided.

The method (2) is commercially disadvantageous because it consists of a number of steps including a step of using an expensive reagent such as N-bromosuccinimide and s step of using a poisonous substance such as sodium cyanide.

Several methods have been known to produce Indoprofen. They can be roughly classified as follows.

(1) The method which comprises reacting an aniline derivative of the general formula

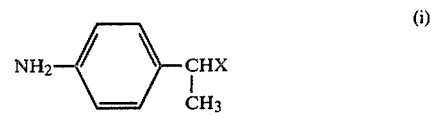

wherein X is carboxyl, alkoxycarbonyl or cyano, with o-cyanobenzyl bromide, phthalide, thiophthalide or phthaldehyde, and hydrolyzing the product with a base or acid (Japanese Patent Publication No. 11627/76).

(2) The method which comprises reacting the compound of formula (i) with phthalic anhydride, a phthalic diester or N-sulfonyl phthalimide to form a compound of the general formula

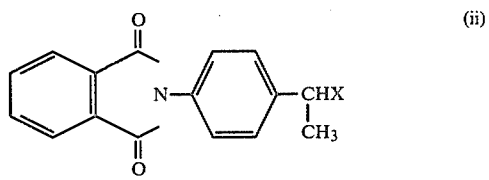

wherein X is carboxyl, alkoxycarbonyl or cyano, reducing the product with a suitable reducing agent to an isoindolinone compound, and if desired, hydrolyzing it (Japanese Patent Publication No. 11627/76 and Japanese Laid-Open Patent Publication No. 65755/76).

(3) The method which comprises reacting the compound of formula (i) with benzaldehyde, reducing the reaction product, reacting the reduction product with phosgene to form a compound of the general formula

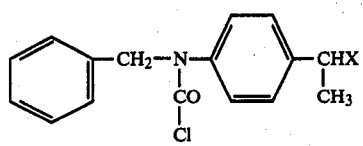 (iii)

subjecting the compound to a Friedel-Crafts reaction to induce its intramolecular cyclization, and if desired, hydrolyzing the product (Japanese Laid-Open Patent Publication No. 57965/73).

All these conventional methods start from the compound of formula (i). This compound is synthesized from toluene through a number of steps. One suggested method for preparing this compound involves chlorinating toluene, reacting it with sodium cyanide to form benzyl cyanide, subjecting the α-position of the product to ethoxycarbonylation, methylation, hydrolysis, and decarboxylation to form α-phenylpropionitrile, nitrating the product, subjecting the nitrile site to solvolysis, and reducing the nitro site [G. Nannini et al., Arzneim. Forsch. (Drug Res.), 23, 1090 (1973)].

The above conventional methods require a number of steps and highly toxic sodium cyanide, and therefore, are very disadvantageous for commercial application.

The conventional methods for producing the other medicines mentioned above also involve some difficulties as in the case of the production of Ibuprofen, Fenoprofen and Indoprofen.

The aforesaid known medicines Ibuprofen, etc., and similar types of various substances can be easily derived with commercial advantage from the compounds of formula (II) corresponding to the groups represented by Ar and R''. The process for production is described in detail below.

The final compound to be produced can be expressed by the following formula

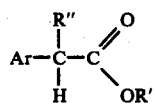 (III)

wherein Ar, R' and R'' are the same as those defined in formula (II).

The starting material used is a compound of formula (II) below.

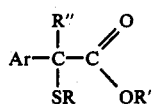 (II)

Reductive desulfurization of the compound of formula (II) can easily afford the compound of formula (III).

The reductive desulfurization, as is seen from the above formula, is a reaction of converting SR group to H.

For example, reductive desulfurization for producing Indoprofen is schematically shown below.

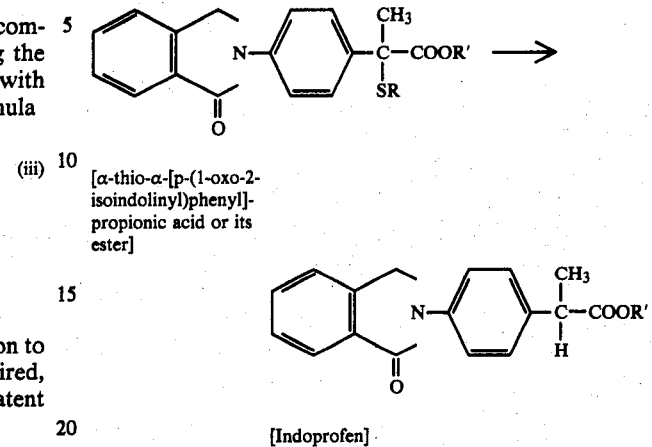

[α-thio-α-[p-(1-oxo-2-isoindolinyl)phenyl]-propionic acid or its ester]

[Indoprofen]

The reductive desulfurization may involve the reduction of a specified group contained in the group Ar concurrently with the conversion of Sr to H. In other words, the production of Indoprofen can also be effected by reductive desulfurization (under acidic conditions) as shown by the following scheme.

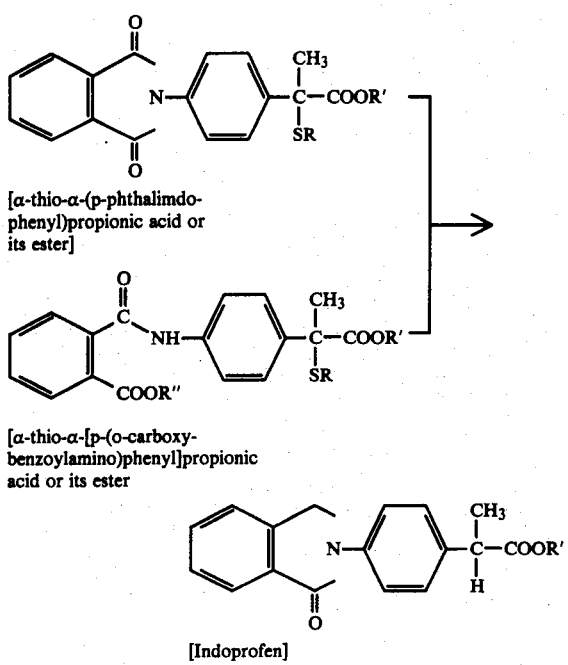

[α-thio-α-(p-phthalimidophenyl)propionic acid or its ester]

[α-thio-α-[p-(o-carboxybenzoylamino)phenyl]propionic acid or its ester

[Indoprofen]

In this way, one carbonyl group contained in the group Ar can concurrently be reduced at the time of the reductive desulfurization.

The reductive desulfurization can be performed by various procedures, for example the reduction with activated nickel metal such as Raney nickel or Urushibara nickel; the reduction using a combination of zinc and a mineral acid or organic acid such as zinc acetic acid, zinc-sulfuric acid or zinc-hydrochloric acid, a combination of tin and a mineral acid such as tin-hydrochloric acid, or a combination such as an amine-alkali metal, or an alcohol-alkali metal; the reduction with aluminum-amalgam; or the reduction with a thiophile such as a thiolate anion or a phosphorous ester.

The reductive desulfurization proceeds smoothly at 0° to 150° C. The reduction, if desired, can be performed in an ordinary organic solvent which does not react with the reducing agent, such as acetic acid, methanol, ethanol, tetrahydrofuran, dioxane, or benzene.

The following examples illustrate the present invention.

First, an experiment of producing a compound of formula (I) as a material for producing a compound of formula (II) is given as Referential Example 1. It is described in the specification of the patent application referred to hereinabove.

REFERENTIAL EXAMPLE 1

Production of methyl α-methylthio(p-isobutylphenyl)acetate:

A mixture of 486 mg of p-isobutylbenzaldehyde and 450 mg of formaldehyde dimethyl mercaptal S-oxide was dissolved in 1 ml of t-butanol, and 2.0 ml of a t-butanol solution (0.608 N) of potassium t-butoxide was added. The mixture was stirred for 12 hours at room temperature. Water (0.5 ml) was added to the reaction mixture, and then 50 ml of methylene chloride was added. The mixture was dried over anhydrous sodium sulfate. The drying agent was separated by filtration, and the filtrate was concentrated under reduced pressure. The oily residue was chromatographed on a column of silica gel using methylene chloride as an eluent to afford 701 mg of 1-methylsufinyl-1-methylthio-2-(p-isobutylphenyl)ethylene in a yield of 87%.

An analytical sample was obtained by short-path distillation (160°–170° C.-bath temperature/0.02 mmHg) of the product.

IR (neat): 1610, 1510, 1470, 1420, 1065, 950, 800 cm$^{-1}$.

NMR (CDCL$_3$): δ0.91 (d, 6H, J=6 Hz), 1.5–2.2 (m, 1H), 2.33 (s, 3H), 2.71 (d, 2H, J=7 Hz), 2.76 (s, 3H), 7.18, 7.81 (A$_2$B$_2$q, 4H), 7.59 (s, 1H).

Elemental analysis for $C_{14}H_{20}OS_2$: Calculated: C, 62.64; H, 7.51; S 23.89%. Found: C, 62.32; H 7.48; S 24.07%.

1-Methylsulfinyl-1-methylthio-2-(p-isobutylphenyl)ethylene (701 mg) was dissolved in 2 ml of chloroform, and 0.50 ml of triethylamine was added. With stirring under ice cooling, 5 ml of a chloroform solution of 380 mg of thionyl chloride was added over the course of 10 minutes. The mixture was further stirred for 30 minutes under ice cooling, and chloroform was added in an amount sufficient to adjust the total amount of the mixture to 30 ml. The mixture was then washed twice with 10 ml of water. The organic layer was dried over anhydrous sodium sulfate, concentrated under reduced pressure, and chromatographed on a Florisil (chromatographic magnesium silicate) column using benzene as an eluent to afford 628 mg of 1,1-bis(methylthio)-2-chloro-2-(p-isobutylphenyl) ethylene as a colorless oil in a yield of 84%.

An analytical sample was obtained by short-path distillation of this product (bath temperature 115°–125° C./0.02 mmHg).

IR (neat): 1505, 1470, 860, 850, 820, 795, 760, 745 cm$^{-1}$.

NMR (CDCl$_3$): δ0.89 (d, 6H, J=6 Hz), 1.6–2.0 (m, 1H), 2.12 (s, 3H), 2.41 (s, 3H), 2.44 (d, 2H, J=7 Hz), 7.0–7.4 (A$_2$B$_2$ q, 4H).

Mass spectrum: m/e 288 (M$^+$+2), 286 (base peak, M$^+$), 245, 243, 57.

Elemental analysis for $C_{14}H_{19}ClS_2$: Calculated: C, 58.61; H, 6.68; Cl, 12.36%. Found: C, 58.69; H, 6.64; Cl, 12.34%.

1,1-Bis(methylthio)-2-chloro-2-(p-isobutylphenyl)ethylene (592 mg) was dissolved in 6 ml of anhydrous methanol, and 0.1 ml of methanol saturated with hydrogen chloride was added. The mixture was heated under reflux for 5 hours, concentrated under reduced pressure, and chromatographed on a silica gel column using benzene as an eluent to afford 471 mg of methyl α-methylthio(p-isobutylphenyl)acetate as a colorless oil in a yield of 90%.

An analytical sample was obtained by short-path distillation of the product (bath temperature 115°–125° C./0.1 mmHg).

IR (neat): 1745, 1150, 1010 cm$^{-1}$.

NMR (CDCl$_3$): δ 0.89 (d, 6H, J=6 Hz), 1.5–2.1 (m, 1H), 2.06 (s, 3H), 2.43 (d, 2H, J=7 Hz), 3.73 (s, 3H), 4.47 (s, 1H), 7.0–7.5 (A$_2$B$_2$q, 4H).

Mass spectrum: m/e 252 (M$^+$), 205, 193 (base peak).

Elemental analysis for $C_{14}H_{20}O_2S$: Calculated: C, 66.63; H, 7.99; S, 12.71%. Found: C, 66.56; H, 7.88; S, 12.47%.

EXAMPLE 1 (FORMULA II)

Methyl α-methylthio(p-isobutylphenyl)acetate (471 mg) was dissolved in 5 ml of anhydrous dimethylformamide, and with stirring under ice cooling, 75 mg (65% content) of sodium hydride was added. Hydrogen evolved immediately. When the mixture was stirred for about 10 minutes, the generation of hydrogen subsided. Methyl iodide (0.25 ml) was added, and the mixture was stirred under ice cooling for 30 minutes, and then at room temperature for 40 minutes. Then, an aqueous solution of ammonium chloride (0.5 g/30 ml) was added, and the mixture was extracted three times with 20 ml of diethyl ether. The organic layer was washed twice with 10 ml of water, dried over anhydrous sodium sulfate, and concentrated under reduced pressure. The residue was chromatographed on a silica gel column using hexane and benzene as eluents to afford 422 mg of methyl α-methylthio-α-(p-isobutylphenyl) propionate as a colorless oil in a yield of 85%.

Boiling point: 118°–120° C./0.1 mmHg.

IR (neat): 1735, 1245, 1105 cm$^{-1}$.

NMR (CDCl$_3$): δ 0.88 (d, 6H, J=6 Hz), 1.78 (s, 3H), 1.97 (s, 3H), 1.5–2.0 (m, 1H), 2.45 (d, 2H, J=7 Hz), 3.76 (s, 3H), 7.0–7.5 (A$_2$B$_2$q, 4H).

Mass spectrum: m/e 266 (M$^+$), 251, 219 (base peak), 207, 191, 159.

Elemental analysis for $C_{15}H_{22}O_2S$: Calculated: C, 67.62; H, 8.33; S, 12.04%. Found: C, 67.54; H, 8.22; S, 12.33%.

EXAMPLE 2 (FORMULA II)

Water (2 ml) and 4 ml of methanol were added to 420 mg of methyl α-methylthio-α-(p-isobutylphenyl)propionate. Then, 280 mg (85% content) of potassium hydroxide was added, and the mixture was stirred at 60° C. for 2.5 hours. The reaction mixture, initially heterogeneous, became uniform. Water (30 ml) was added, and the mixture was extracted with 10 ml of methylene chloride. The aqueous layer was acidified with conc. hydrochloric acid to a pH of 1, and extracted three times with 20 ml of diethyl ether. The organic layer was dried over anhydrous sodium sulfate, and concentrated under reduced pressure to remove the diethyl ether. Thus, 394 mg of crude α-methylthio-α-(p-isobutylphenyl)propionic acid was obtained as an oil in a yield of 99%. The oil soon crystallized, and recrystallization from water-methanol afforded colorless crystals having a melting point of 89° to 92° C.

IR (KBr): 3000–2500, 1695, 1295, 1275, 940 cm$^{-1}$.

NMR (CDCl$_3$): δ 0.90 (d, 6H, J=6 Hz), 1.5–2.0 (m, 1H), 1.80 (s, 3H), 2.02 (s, 3H), 2.46 (d, 2H, J=7 Hz), 7.0–7.5 (A$_2$B$_2$q, 4H), 13.9 (s, 1H).

Elemental analysis for C$_{14}$H$_{20}$O$_2$S: Calculated: C, 66.63; H, 7.99; S, 12.71%. Found: C, 66.85; H, 7.76; S, 12.67%.

EXAMPLE 3

α-Methylthio-α-(p-isobutylphenyl)propionic acid (387 mg) was dissolved in 3 ml of acetic acid, and 200 mg of zinc powder was added. The mixture was heated under reflux for 2 hours. Furthermore, 200 mg of zinc powder was added, and the mixture was heated under reflux for 18 hours. The zinc powder which agglomerated was pulverized, and the mixture was again heated under reflux for 20 hours. Water (30 ml) and 20 ml of diethyl ether were added, and the insoluble matter was separated by filtration. Then, conc. hydrochloric acid was added to adjust the pH of the mixture to 1, and it was extracted four times with 20 ml of diethyl ether. The organic layer was washed with 10 ml of water, dried over anhydrous sodium sulfate, and concentrated under reduced pressure to remove the diethyl ether and acetic acid. Thus, 319 mg of α-(p-isobutylphenyl)propionic acid was obtained as an oil which crystallized soon. Recrystallization from hexane afforded colorless crystals having a melting point of 74° to 76° C. The IR and NMR spectra of this product were identical with those of the authentic sample.

EXAMPLE 4 (FORMULA II)

Methyl α-methylthio(m-phenoxyphenyl)acetate (1.963 g) was dissolved in anhydrous dimethylformamide, and under ice cooling, 280 mg (65% content) of sodium hydride was added. The mixture was stirred for 10 minutes. Then, 0.60 ml of methyl iodide was added, and the mixture was stirred under ice cooling for 5 minutes and then at room temperature for 30 minutes. After adding an aqueous solution of ammonium chloride (500 mg/40 ml), the reaction mixture was extracted three times with 20 ml of diethyl ether. The organic layer was washed three times with 10 ml of water, dried over anhydrous sodium sulfate, and concentrated under reduced pressure. The residue was chromatographed on a silica gel column using hexane and benzene as eluents to afford 1.930 g of methyl α-methylthio-α-(m-phenoxyphenyl)propionate as an oil in a yield of 94%. Distillation of this substance gave a fraction boiling at 147°–149° C./0.08 mmHg.

IR (neat): 1735, 1585, 1490, 1240, 1110, 930, 760, 695 cm$^{-1}$.

NMR (CDCl$_3$): δ 1.74 (s, 3H), 1.96 (s, 3H), 3.60 (s, 3H), 6.7–7.4 (m, 9H).

Elemental analysis for C$_{17}$H$_{18}$O$_3$S: Calculated: C, 67.52; H, 6.00; S, 10.60%. Found: C, 67.56; H, 5.88; S, 10.47%.

EXAMPLE 5 (FORMULA II)

Methanol (4 ml) and 2 ml of water were added to 663 mg of methyl α-methylthio-α-(m-phenoxyphenyl)propionate, and then 300 mg of sodium hydroxide was added. The mixture was heated under reflux for 2 hours, diluted with 30 ml of water, and extracted with 10 ml of diethyl ether. The aqueous layer was acidified with about 1 ml of conc. hydrochloric acid, and extracted three times with 20 ml of diethyl ether. The organic layer was washed with 10 ml of water, and dried over anhydrous sodium sulfate. Concentration under reduced pressure gave 628 mg of α-methylthio-α-(m-phenoxyphenyl)propionic acid as an oil in a yield of 99%. This product crystallized on standing at room temperature. Recrystallization from hexane and carbon tetrachloride afforded colorless crystals having a melting point of 87° to 88° C.

IR (KBr): 3100–2500, 1695, 1595, 1585, 1490, 1255, 950, 750, 705, 690 cm$^{-1}$.

NMR (CDCl$_3$): δ 1.78 (s, 3H), 2.04 (s, 3H), 6.8–7.4 (m, 9H), 10.30 (broad s, 1H).

Elemental analysis for C$_{16}$H$_{16}$O$_3$S: Calculated: C, 66.64; H, 5.59; S, 11.12%. Found: C, 66.39; H, 5.52; S, 11.04%.

EXAMPLE 6

Water (1.5 ml) and 1.5 ml of conc. hydrochloric acid were added to 432 mg of α-methylthio-α-(m-phenoxyphenyl)propionic acid, and then 300 mg of zinc powder was added. With stirring, the mixture was heated under reflux for 2.5 hours. Water (10 ml) and 30 ml of diethyl ether were added to the reaction mixture. The insoluble matter was separated by filtration. The filtrate was extracted three times with 30 ml of diethyl ether. The organic layer was washed with 10 ml of water, and dried over anhydrous sodium sulfate. The solvent was removed under reduced pressure to afford 364 mg of α-(m-phenoxyphenyl)propionic acid as an oil.

An analytical sample was obtained by short-path distillation of this product (bath temperature 160°–170° C./0.02 mmHg) [lit. boiling point: 168°–171° C./0.11 mmHg (U.S. Pat. No. 3,600,437)]

IR (neat): 3500–2800, 1715, 1590, 1490, 1250, 935, 760, 695 cm$^{-1}$.

NMR (CDCl$_3$): δ 1.44 (d, 3H, J=7 Hz), 3.63 (g, 1H, J=7 Hz), 6.7–7.4 (m, 9H), 11.67 (broad s, 1H).

Elemental analysis for C$_{15}$H$_{14}$O$_3$: Calculated: C, 74.36; H, 5.83%. Found: C, 74.10; H, 5.71%.

EXAMPLE 7

Methyl α-methylthio-α-(m-phenoxyphenyl)propionate (302 mg) was dissolved in 2 ml of acetic acid, and 16 mg of anhydrous copper sulfate and 150 mg of zinc powder were added. With stirring, the mixture was heated under reflux for 9 hours. Furthermore, 50 mg of zinc powder was added, and the mixture was heated under reflux for 2 hours. Diethyl ether (60 mg) was added, and the insoluble matter was separated by filtration. The filtrate was washed twice with 10 ml of water and dried over anhydrous sodium sulfate. The solvent was removed under reduced pressure, and the residue was subjected to short-path distillation (bath temperature 140°–160° C./0.02 mmHg) to afford 249 mg of methyl α-(m-phenoxyphenyl)propionate as a colorless oil in a yield of 97%.

IR (neat): 1740, 1585, 1490, 1250, 925, 760, 690 cm$^{-1}$.

NMR (CDCl$_3$): δ 1.45 (d, 3H, J=7 Hz), 3.60 (s, 3H), 3.64 (q, 1H, J=7 Hz), 6.7–7.4 (m, 9H).

Elemental analysis for C$_{16}$H$_{16}$O$_3$: Calculated: C, 74.98; H, 6.29%. Found: C, 74.84; H, 6.27%.

EXAMPLE 8 (FORMULA II)

In 2 ml of anhydrous dimethyl sulfoxide was dissolved 600 mg of methyl α-methylthio(m-phenoxyphenyl) acetate, and 120 mg of sodium amide was added. The mixture was stirred at about 30° C. for 2.5 hours. Then, 0.20 ml of methyl iodide was added, and the mixture was stirred for 40 minutes at room temperature. An aqueous solution of ammonium chloride (0.5 g/20 ml) was added, and the mixture was extracted three times with 25 ml of diethyl ether. The organic layer was washed three times with 20 ml of water, dried over anhydrous sodium sulfate, and concentrated under reduced pressure. The residue was chromatographed on a silica gel column using benzene as an eluent to afford 354 mg of methyl α-methylthio-α-(m-phenoxyphenyl)-propionate in a yield of 59%.

EXAMPLE 9

Methyl α-methylthio-α-(m-phenoxyphenyl)propionate (608 mg) was dissolved in 2 ml of anhydrous methanol, and 2.0 ml (2.34 M) of a methanol solution of a sodium salt of methyl mercaptan was added, and the mixture was heated under reflux for 17 hours. After cooling, an aqueous solution of ammonium chloride was added, and the mixture was extracted three times with 20 ml of diethyl ether. The extract was washed with 20 ml of a saturated aqueous solution of sodium hydrogen carbonate, dried over anhydrous sodium sulfate, and concentrated under reduced pressure to afford 320 mg of a colorless oily residue. From an NMR analysis, this product was determined to be a mixture of methyl α-methylthio-α-(m-phenoxyphenyl)propionate and methyl α-(m-phenoxyphenyl)propionate, and the yield of the methyl α-(m-phenoxyphenyl)propionate was calculated as 55%.

The washing was adjusted to pH 1 with conc. hydrochloric acid, and extracted three times with 18 ml of diethyl ether. The organic layer was washed with 20 ml of water, and then dried over anhydrous sodium sulfate. Concentration under reduced pressure gave 170 mg of a residue. The residue was determined to be a mixture of α-methylthio-α-(m-phenoxyphenyl)propionic acid and α-(m-phenoxyphenyl)propionic acid. The yield of the α-(m-phenoxyphenyl)propionic acid was calculated as 23%.

EXAMPLE 10

α-Methylthio-α-(m-phenoxyphenyl)propionic acid (288 mg) was dissolved in a mixture of 1 ml of t-butanol and 4 ml of tetrahydrofuran, and 100 mg of metallic sodium was added. The mixture was stirred at room temperature for 10 minutes. The mixture was heated under reflux for an additional 1.5 hours with stirring. After cooling, a small amount of ethanol was added to consume the unreacted metallic sodium completely. Water (20 ml) was added, and the pH of the mixture was adjusted to 1 with conc. hydrochloric acid. The mixture was extracted three times with 27 ml of diethyl ether. The extract was washed twice with 20 ml of water, dried over anhydrous magnesium sulfate, concentrated under reduced pressure, and chromatographed on a silica gel column using methylene chloride as an eluent to afford 234 mg of α-(m-phenoxyphenyl)propionic acid in a yield of 97%.

EXAMPLE 11

Metallic sodium (30 mg) was added to 5 ml of anhydrous ethanol to dissolve it completely. Thus, 300 mg of α-methylthio-α-(m-phenoxyphenyl)propionic acid was added, and the mixture was cooled with ice. Then, 100 mg of metallic sodium was added, and the mixture was stirred for 30 minutes. For an additional 40 minutes, the mixture was heated under reflux. After cooling, the mixture was diluted with 20 ml of water, and conc. hydrochloric acid was added to adjust its pH to 1. The mixture was extracted three times with 25 ml of diethyl ether. The extract was dried over anhydrous sodium sulfate, and concentrated under reduced pressure to afford 293 mg of a residue. From an NMR analysis, the product was determined to be a mixture of α-methylthio-α-(m-phenoxyphenyl)propionic acid and α-(m-phenoxyphenyl)propionic acid, and the yield of the α-(m-phenoxyphenyl)propionic acid was calculated as 24%.

EXAMPLE 12

Water (4 ml) was added to 10 g of zinc powder, and the mixture was heated over a boiling water bath and vigorously stirred. Then, 10 ml of a hot water solution of 4 g of nickel chloride hexahydrate was added in the course of 2 to 3 seconds. A vigorous reaction occurred, and a black precipitate was formed. The precipitate was washed with hot water, and stored in methanol. By using the nickel-zinc alloy obtained, reduction was performed in the following manner.

α-Methylthio-α-(m-phenoxyphenyl)propionic acid (300 mg) was added to 3 ml of a 10% aqueous solution of potassium hydroxide, and 200 mg of the nickel-zinc alloy obtained by the procedure given above was added. The mixture was heated under reflux for 45 minutes with stirring. After cooling, the insoluble matter was separated by filtration. The filtrate was adjusted to pH 1 with conc. hydrochloric acid, and extracted three times with 30 ml of diethyl ether. The organic layer was dried over anhydrous sodium sulfate, and concentrated under reduced pressure to afford 301 mg of an oily residue. From an NMR analysis, this product was determined to be a mixture of α-(m-phenoxyphenyl)propionic acid and α-methylthio-α-(m-phenoxyphenyl)propionic acid, and the yield of the α-(m-phenoxyphenyl)propionic acid was calculated as 14%.

EXAMPLE 13 (FORMULA II)

α-Methylthio-α-(m-phenoxyphenyl)acetic acid (390 mg) was dissolved in 2 ml of anhydrous dimethylformamide, and with ice cooling, 120 mg (65% content) of sodium hydride was added. The mixture was stirred for 30 minutes. Then, 0.3 ml of methyl iodide was added, and after cooling with ice for 5 minutes, the mixture was stirred at room temperature for 2.5 hours. After adding an aqueous solution of ammonium chloride (1 g/40 ml), the mixture was extracted three times with 25 ml of diethyl ether. The organic layer was washed with 20 ml of water, dried over anhydrous magnesium sulfate, and concentrated under reduced pressure. The residue was chromatographed on a column of silica gel using benzene as an eluent to afford 278 mg of methyl α-methylthio-α-(m-phenoxyphenyl)propionate in a yield of 65%.

EXAMPLE 14 (FORMULA II)

Methyl α-phenylthio(m-phenoxyphenyl)acetate (521 mg) was dissolved in 2 ml of anhydrous dimethylformamide. After cooling with ice, 65 mg (65% content) of sodium hydride was added, and the mixture was stirred for 30 minutes. Then, 0.15 ml of methyl iodide was added, and the mixture was stirred for 5 minutes with ice cooling and then for 2 hours at room temperature. After an aqueous solution of ammonium chloride (1 g/40 ml) was added, the mixture was extracted three times with 40 ml of diethyl ether. The organic layer was washed twice with 20 ml of water, dried with anhydrous magnesium sulfate, and concentrated under reduced pressure. The residue was chromatographed on a silica gel column using benzene as an eluent to afford 522 mg of methyl α-phenylthio-α-(m-phenoxyphenyl)propionate as an oil in a yield of 96%.

IR (neat), 1737, 1587, 1490, 1440, 1245, 1115, 935, 760, 698 cm$^{-1}$.

NMR (CDCl$_3$): δ 1.75 (s, 3H), 3.58 (s, 3H), 6.7–7.4 (m, 14H).

Mass spectrum: m/e 364 (M+), 256, 255 (base peak), 227, 195.

EXAMPLE 15

Methyl α-phenylthio-α-(m-phenoxyphenyl)propionate (210 mg) was dissolved in 1 ml of ethanol. An ethanol suspension (5 ml) of 2 cc of Raney nickel (W-II) was added, and the mixture was stirred at room temperature for 5 hours. The reaction mixture was filtered, and the insoluble matter was washed with 50 ml of methanol. The filtrate and the washing were combined, and concentrated under reduced pressure. Methylene chloride (30 ml) was added to the residue, and the insoluble matter was separated by filtration. The filtrate was concentrated under reduced pressure, and the residue was chromatographed on a column of silica gel using benzene as an eluent to afford 134 mg of methyl α-(m-phenoxyphenyl)propionate in a yield of 90%.

EXAMPLE 16 (FORMULA II)

Methyl α-methylthio-(m-phenoxyphenyl)acetate (1.77 g) was dissolved in 10 ml of dimethylformamide, and with ice cooling, 260 mg (65% content) of sodium hydride was added. The mixture was stirred for 30 minutes. Then, 0.70 ml of isopropyl bromide was added, and with ice cooling for 3 minutes, the mixture was stirred at room temperature for 2.5 hours. After adding an aqueous solution of ammonium chloride (1 g/40 ml), the mixture was extracted three times with 50 ml of diethyl ether. The organic layer was washed twice with 20 ml of water, dried over anhydrous sodium sulfate, and concentrated under reduced pressure. The residue was chromatographed on a silica gel column using benzene as an eluent to afford 1.25 g of methyl α-methylthio-α-(m-phenoxyphenyl)isovalerate in a yield of 62%.

An analytical sample was obtained by short-path distillation (bath temperature 160°–165° C./0.01 mmHg) of this product.

IR (neat): 3100–2800, 1730, 1585, 1490, 1435, 1235, 1165, 1030, 757, 713, 697 cm$^{-1}$.

NMR (CDCl$_3$): δ 0.90 (d, 3H), 0.92 (d, 3H, J=7 Hz), 1.92 (s, 3H), 2.57 (septet, 1H, J=7 Hz), 3.72 (s, 3H), 6.7–7.4 (m, 9H).

Elemental analysis for C$_{19}$H$_{22}$O$_3$S: Calculated: C, 69.09; H, 6.66; S, 9.69%. Found: C, 68.98; H, 6.49; S, 9.63%.

EXAMPLE 17

Methyl α-methylthio-α-(m-phenoxyphenyl) isovalerate (702 mg) was dissolved in 5 ml of acetic acid, and 50 mg of anhydrous copper sulfate and 500 mg of zinc powder were added. The mixture was heated under reflux for 23 hours. Diethyl ether (80 ml) was added, and the insoluble matter was separated by filtration. The filtrate was washed twice with 25 ml of water, dried over anhydrous magnesium sulfate, and concentrated under reduced pressure. The residue was chromatographed on a silica gel column using benzene as an eluent to afford 531 mg of methyl α-(m-phenoxyphenyl)isovalerate in a yield of 88%.

An analytical sample was obtained by short-path distillation (bath temperature 150°–155° C./0.03 mmHg) of this product.

IR (neat): 3100–2800, 1740, 1590, 1490, 1450 1255, 1165, 760, 695 cm$^{-1}$.

NMR (CDCl$_3$): δ 0.75 (d, 3H, J=7 Hz), 1.02 (d, 3H, J=7 Hz), 2.3 (m, 1H), 3.13 (d, 1H, J=11 Hz), 3.62 (s, 3H), 6.8–7.4 (m, 9H).

Elemental analysis for C$_{18}$H$_{20}$O$_3$: Calculated: C, 76.05; H, 7.04%. Found: C, 75.92; H, 6.90%.

EXAMPLE 18 (FORMULA II)

Methyl α-methylthio(p-aminophenyl)acetate (760 mg) and 533 mg of phthalic anhydride were dissolved in 8 ml of acetic acid, and the solution was heated under reflux for 4 hours. The reaction mixture was concentrated under reduced pressure, and 100 ml of an aqueous solution of sodium bicarbonate was added. The mixture was extracted once with 20 ml of methylene chloride, and then twice with 10 ml of methylene chloride. The organic layer was dried over anhydrous sodium sulfate, and concentrated under reduced pressure to afford 1.222 g of methyl α-methylthio(p-phthalimidophenyl)acetate as colorless crystals in a yield of 99.5%.

Melting point: 168°–169° C. (from methanol)

IR (KBr): 1785 (w), 1765 (w), 1740, 1715 cm$^{-1}$

NMR (CDCl$_3$): δ 2.11 (s, 3H), 3.76 (s, 3H), 4.55 (s, 1H), 7.48 (d, 2H, J=8.5 Hz), 7.60 (d, 2H, J=8.5 Hz), 7.74–8.00 (m, 4H).

Elemental analysis for C$_{18}$H$_{15}$NO$_4$S: Calculated: C, 63.33; H, 4.43; N, 4.10%. Found: C, 63.27; H, 4.50; N, 4.01%.

Methyl α-methylthio(p-phthalimidophenyl)acetate (978 mg) was dissolved in 10 ml of anhydrous dimethylformamide, and under ice cooling, 120 mg of sodium hydride (65% content) was added. The mixture was stirred for 10 minutes. Then, 0.25 ml of methyl iodide was gradually added. The temperature was raised to room temperature, and the mixture was stirred for 5 minutes. An aqueous solution of ammonium chloride (500 mg/30 ml) was added, and the mixture was extracted four times with 20 ml of methylene chloride. The organic layer was washed with 10 ml of water, dried over anhydrous sodium sulfate, and then concentrated under reduced pressure. The residue was washed with 20 ml of hexane to afford 788 mg of methyl α-methylthio-α-(p-phthalimidophenyl)propionate as colorless crystals in a yield of 77%.

Melting point: 142°–145° C. (from ethanol)

IR (KBr): 1790, 1770, 1735, 1720, 1510, 1390, 1250, 1105, 890, 725 cm$^{-1}$

NMR (CDCl$_3$): δ 1.79 (s, 3H), 1.99 (3, 3H), 3.74 (s, 3H), 7.3–8.0 (m, 8H).

Mass spectrum: m/e 355 (M+), 308 (base peak), 2.96, 280, 248.

Elemental analysis for C$_{19}$H$_{17}$NO$_4$S: Calculated: C, 64.21; H, 4.82; N, 3.94; S, 9.02%. Found: C, 63.92; H, 4.65; N, 3.79; S, 9.32%.

EXAMPLE 19

Methanol (1 ml) and 1 ml of water were added to 178 mg of methyl α-methylthio-α-(p-phthalimidophenyl) propionate. Sodium hydroxide (80 mg) was added, and the mixture was stirred for 1 hour at room temperature, and then for 30 minutes at 50° to 60° C. Adjustment of the pH of the reaction mixture to 1 with conc. hydrochloric acid resulted in the precipitation of colorless crystals. The crystals were collected by filtration, washed with 15 ml of water, and dried to afford 152 mg of α-methylthio-α-(p-(o-carboxybezoylamino)-phenyl)proionic acid in a yield of 84%.

Decomposition point of colorless crystals: 140°–158° C. (from methanol-water)

IR (KBr): 3400–2700, 1730, 1700, 1600, 1540, 1410, 1235 cm$^{-1}$.

NMR (CD$_3$OD): δ 1.77 (s, 3H), 1.98 (s, 3H), 7.3–8.2 (m, 8H).

Elemental analysis for C$_{18}$H$_{17}$NO$_5$S: Calculated: C, 60.12; H, 4.77; N, 3.90%. Found: C, 60.02; H, 4.63; N, 3.64%.

EXAMPLE 20 (FORMULA II)

α-Methylthio-α-(p-(o-carboxybenzoylamino)-phenyl)propionic acid (146 mg) was dissolved in 1 ml of acetic acid, and the solution was heated under reflux for 3 hours. Acetic acid was removed under reduced pressure to afford 134 mg of α-methylthio-α-(p-phthalimidophenyl)propionic acid as colorless crystals.

Melting point: 202°–204° C. (from methanol-water)

IR (KBr): 3100°–2700, 1790, 1765, 1715 (broad), 1515, 1380, 1290, 1225, 1080, 885, 720 cm$^{-1}$.

NMR (d$_6$-DMSO): δ 1.75 (s, 3H), 1.94 (s, 3H), 7.50 (A$_2$B$_{2q}$, 4H), 7.89 (A$_2$B$_{2q}$, 4H), 12.2–13.1 (broad, 1H).

EXAMPLE 21

α-Methylthio-α-(p-(o-carboxybenzoylamino)-phenyl)propionic acid (130 mg), 300 mg of zinc powder and 20 mg of of anhydrous copper sulfate were added to 1.5 ml of acetic acid and the resulting mixture was heated under reflux for 5 hours with stirring. After cooling, 30 ml of methylene chloride and 20 ml of water were added. The insoluble precipitate was separated by filtration. The filtrate was acidified to a pH of 1 with conc. hydrochloric acid, and extracted three times with 20 ml of methylene chloride. The organic layer was washed with 20 ml of water, and dried over anhydrous sodium sulfate. The solvent was evaporated under reduced pressure to afford 86 mg of α-[p-1-oxo-2-isoindolinyl)phenyl]propionic acid in a yield of 85%.

EXAMPLE 22

Methyl α-methylthio-α-(p-phthalimidophenyl)propionate (355 mg), 600 mg of zinc powder and 32 mg of anhydrous copper sulfate were heated under reflux for 5 hours in 3 ml of acetic acid. Methylene chloride (30 ml) was added, and the insoluble matter was separated by filtration and washed with 20 ml of methylene chloride. The filtrate and the washing were combined, washed twice with 10 ml of water, and dried over anhydrous sodium sulfate. The solvent was evaporated off under reduced pressure. The residue was chromatographed on a silica gel column using methylene chloride as an eluent to afford 245 mg of methyl α-[p-1-oxo-2-isoindolinyl)phenyl]propionate as colorless crystals in a yield of 83%.

Melting point: 127.5°–128.5° C. (from methanol)

IR (KBr): 1740, 1680, 1515, 1470, 1390, 1335, 1310, 1165, 1155, 740 cm$^{-1}$.

NMR (CDCl$_3$): δ1.47 (d, 3H, J=7 Hz), 3.60 (s, 3H), 3.68 (q, 1H, J=7 Hz), 4.76 (s, 2H), 7.2–7.9 (m, 8H).

Elemental analysis for C$_{18}$H$_{17}$NO$_3$: Calculated: C, 73.20; H, 5.80; N, 4.73%. Found: C, 72.97; H, 5.69; N, 4.65%.

EXAMPLE 23

α-Methylthio-α-(p-phthalimidophenyl)propionic acid (123 mg), 300 mg of zinc powder and 16 mg of anhydrous copper sulfate were stirred in 1.5 ml of acetic acid at the refluxing temperature for 5 hours. After cooling, 30 ml of methylene chloride and 20 ml of water were added, and the insoluble precipitate was separated by filtration. The filtrate was adjusted to pH 1 with conc. hydrochloric acid, and extracted three times with 20 ml of methylene chloride. The organic layer was washed with 10 ml of water, and dried with anhydrous sodium sulfate, and the solvent was evaporated off under reduced pressure to afford 99 mg of α-[p-(1-oxo-2-isoindolinyl)phenyl]propionic acid in a yield of 98%.

EXAMPLE 24 (FORMULA II)

Anhydrous dimethylformamide (7 ml) was added to 256 mg of methyl α-methylthio[p-(1-oxo-2-isoindolinyl)phenyl]acetate. With ice cooling and stirring, 35 mg (65% content) of sodium hydroxide was added. The mixture was stirred for 10 minutes at room temperature and again cooled with ice. Methyl iodide (0.1 ml) was added, and the mixture was stirred for 5 minutes. Addition of an aqueous solution of ammonium chloride (100 mg/30 ml) resulted in the precipitation of colorless crystals. The crystals were collected by filtration, washed with 20 ml of water and then with 10 ml of n-hexane, and dried to afford 191 mg of methyl α-methylthio-α-[p-(1-oxo-2-isoindolinyl)phenyl]propionate.

The filtrate and the washing were combined and extracted three times with 20 ml of methylene chloride. The extract was washed with 10 ml of water, dried over anhydrous sodium sulfate, and concentrated under reduced pressure. The residue was wahsed with 10 ml of n-hexane to afford 39 mg of methyl α-methylthio-α-[p-(1-oxo-2-indolinyl)phenyl]propionate. The total amount of the product was 230 mg (yield 86%).

Melting point: 156°–159° C. (from methanol)

IR (KBr): 1730, 1685, 1395, 1245, 1100, 730 cm$^{-1}$.

NMR (CDCl$_3$): δ1.82 (s, 3H), 2.00 (s, 3H), 3.78 (s, 3H), 4.82 (s, 2H), 7.3–7.7 (m, 5H), 7.7–8.0 (m, 3H).

Elemental analysis for C$_{19}$H$_{19}$NO$_3$S: Calculated: C, 66.84; H, 5.61; N, 4.10; S, 9.39%. Found: C, 66.60; H, 5.42; N, 3.83; S, 9.21%.

EXAMPLE 25 (FORMULA II)

Methanol (2 ml) and 1 ml of water were added to 170 mg of methyl α-methylthio-α-[p-(1-oxo-2-isoindolinyl)phenyl]propionate, and 150 mg of sodium hydroxide was added. The mixture was heated under reflux for 2 hours. Adjustment of its pH to 1 with conc. hydrochloric acid resulted in the precipitation of colorless crystals. The colorless crystals were collected by filtration, washed with 20 ml of water, and dried to afford 151 mg of α-methylthio-α-[p-(1-oxo-2-isoindolinyl)phenyl]propionic acid in a yield of 93%.

Melting point: 196°–199° C. (from methanol)

IR (KBr): 3100–2700, 1725, 1695, 1650, 1515, 1395, 1310, 1225, 740 cm$^{-1}$.

NMR (d$_6$-DMSO): δ1.77 (s, 3H), 1.96 (s, 3H), 5.02 (s, 2H), 7.4–8.0 (m, 8H).

Elemental analysis for C$_{18}$H$_{17}$NO$_3$S: Calculated: C, 66.03; H, 5.24; N, 4.28; S, 9.79%. Found: C, 65.93; H, 5.14; N, 4.11; S. 10.11%.

EXAMPLE 26

Acetic acid (2 ml), 8 mg of anhydrous copper sulfate and 120 mg of zinc powder were added to 148 mg of α-methylthio-α-[p-(1-oxo-2-isoindolinyl)phenyl]propionic acid, and the mixture was heated under reflux for 5 hours. Conc. hydrochloric acid was added to adjust the pH of the mixture to 1. Water (20 ml) and 20 ml of methylene chloride were added, and the insoluble matter was separated by filtration. The filtrate was extracted four times with 20 ml of methylene chloride. The organic layer was washed with 10 ml of water, dried over anhydrous sodium sulfate, and concentrated under reduced pressure to afford 124 mg of α-[p-(1-oxo-2-isoindolinyl)phenyl]propionic acid as colorless crystals in a yield of 99.8%. Recrystallization of the resulting product from ethanol afforded crystals having a melting point of 205° to 208° C.

Elemental analysis for $C_{17}H_{15}NO_3$: Calculated: C, 72.58; H. 5.38; N, 4.98%. Found: C, 72.52; H, 5.35; N, 4.84%.

EXAMPLE 27 (FORMULA II)

Methyl α-methylthio(3-chloro-4-phthalimidophenyl)acetate was dissolved in 4.0 ml of dimethylformamide, and with ice cooling and stirring, 82 mg (65% content) of sodium hydride was added. The mixture was stirred for 10 minutes. With ice cooling, 0.2 ml of methyl iodide was added, but the deep red color did not vanish. Hence, 0.2 ml of methyl iodide was further added, and the mixture was stirred for about 1.5 hours at room temperature. The color of the solution became lighter, and turned orange. To the reaction solution was added 20 ml of an aqueous solution of ammonium chloride, and the mixture was extracted twice with 10 ml of methylene chloride. The extract was dried over anhydrous sodium sulfate, and concentrated under reduced pressure. The residual orange oil was chromatographed on a column of Florisil using methylene chloride as an eluent to afford 0.453 g (68%) of methyl α-methylthio-α-(3-chloro-4-phthalimidophenyl)propionate as colorless crystals.

Melting point: 141°–142° C.

IR (nujol): 1785, 1765 (W), 1730, 1495, 1105, 1080, 880, 720 cm$^{-1}$.

NMR (CDCl$_3$): δ1.83 (s, 3H), 2.06 (s, 3H), 3.82 (s, 3H), 7.38 (d, 1H, J=8.5 Hz), 7.55 (dd, 1H, J=2 and 8.5 Hz), 7.74 (d, 1H, J=2 Hz), 7.76–8.06 (m, 4H).

Elemental analysis for $C_{19}H_{16}ClNO_4S$: Calculated: C, 58.54; H, 4.14; N, 3.59; S, 8.22; Cl, 9.09%. Found: C, 58.50; H, 4.08; N, 3.60; S, 8.25; Cl, 9.10%.

EXAMPLE 28 (FORMULA II)

Methyl α-methylthio-α-(3-chloro-4-phthalimidophenyl)propionate was suspended in 7 ml of methanol, and 97 mg of hydrazine hydrate was added. The mixture was stirred at room temperature, and then heated under reflux for 1 hour. The mixture was concentrated under reduced pressure, and an aqueous solution of ammonium chloride and methylene chloride were added. The organic layer was separated, and dried over anhydrous sodium sulfate. Concentration under reduced pressure yielded 231 mg of methyl α-methylthio-α-(3-chloro-4-aminophenyl)propionate as a pale yellow oil. Yield 92%.

Boiling point: 161°–163° C./0.45 mmHg

IR (neat): 3490, 3300, 1730, 1625, 1603, 1245, 1105 cm$^{-1}$

NMR (CDCl$_3$): δ1.74 (s, 3H), 1.93 (s, 3H), 3.70 (s, 3H), 4.0–4.1 (broad, 2H), 6.65 (d, 1H, J=8.5 Hz), 7.09 (dd, 1H, J=8.5 and 2 Hz), 7.31 (d, 1H, J=2 Hz).

Elemental analysis for $C_{11}H_{14}ClNO_2S$: Calculated: C, 50.86; H, 5.43; N, 5.39; S, 12.34; Cl, 13.65%. Found: C, 50.91; H, 5.51; N, 5.48; S, 12.24; Cl, 13.58%.

EXAMPLE 29

Methyl α-methylthio-α-(3-chloro-4-aminophenyl)propionate (380 mg) was dissolved in 4 ml of acetic acid, and an intimate mixture of 406 mg of zinc powder and 1.5 mg of anhydrous copper sulfate was added. The entire mixture was heated under reflux for 1 hour. Water (40 ml) and 15 ml of diethyl ether were added to the reaction mixture. The insoluble matter was separated by filtration, and then the organic layer was separated. Furthermore, the aqueous layer was extracted with 5 ml of diethyl ether. The organic layer and the extract were combined, washed with 15 ml of a saturated aqueous solution of sodium hydrogen carbonate, dried over anhydrous magnesium sulfate, and concentrated under reduced pressure to afford 299 mg of methyl α-(3-chloro-4-aminophenyl)propionate in a yield of 95.6% as a colorless oil.

IR (neat): 3490, 3400, 1735, 1630, 1507, 1210, 1170 cm$^{-1}$.

NMR (CDCl$_3$): δ1.40 (d, 3H, J=7 Hz), 3.52 (q, 1H, J=7 Hz), 3.56 (s, 3H), 4.0 (broad, 2H), 6.60 (d, 1H, J=8 Hz), 6.90 (dd, 1H, J=8 and 2 Hz), 7.12 (d, 1H, J=2 Hz).

Elemental analysis for $C_{10}H_{12}ClNO_2$: Calculated: C, 56.22; H, 5.66; N, 6.56; Cl, 16.59%. Found: C, 56.00; H, 5.52; N, 6.73; Cl, 16.73%.

EXAMPLE 30 (FORMULA II)

Methyl α-methylthio(3-chloro-4-piperidinophenyl)acetate (2.524 g) was dissolved in 15 ml of N,N-dimethylformamide, and under ice cooling, 420 mg of sodium hydride (65% content) was added. The mixture was stirred for 15 minutes, and then 3.5 ml of methyl iodide was added. The mixture was stirred for 2 minutes under ice cooling, and then for 1 hour and 15 minutes at room temperature. Then 60 ml of a saturated aqueous solution of ammonium chloride was added, and the mixture was extracted twice with 25 ml of methylene chloride. The extract was dried over anhydrous sodium sulfate, and concentrated under reduced pressure to afford a brown oily product. The oily product was chromatographed on a column of Florisil using n-hexane-benzene as an eluent to afford 2.012 g (76.2%) of methyl α-methylthio-α-(3-chloro-4-piperidinophenyl)propionate. On standing overnight, the product crystallized.

Melting point: 83.5°–85.0° C. (from methanol)

IR (KBr): 1243, 1728, 2530 cm$^{-1}$.

NMR (CDCl$_3$): δ1.40–1.90 (m, 6H), 1.74 (s, 3H), 1.95 (s, 3H), 2.80–3.10 (m, 4H), 3.72 (s, 3H), 6.93 (d, 1H, J=8 Hz), 7.24 (dd, 1H, J=2 and 8 Hz), 7.41 (d, 1H, J=2 Hz).

EXAMPLE 31 (FORMULA II)

Methyl α-methylthio-α-(6-methoxy-2-naphthyl)acetate (420 mg) was dissolved in 5 ml of dimethylformamide, and 60 mg (65% content) of sodium hydride was added. The mixture was stirred at room temperature for 10 minutes. Then, 0.20 ml of methyl iodide was added, and the mixture was stirred at room temperature for 30 minutes. An aqueous solution of ammonium chloride (0.5 g/30 ml) was added and the mixture was extracted three times with 20 ml of diethyl ether. The organic layer was washed twice with 10 ml of water and dried over anhydrous sodium sulfate. The solvent was evaporated off under reduced pressure, and the residue was chromatographed on a silica gel using benzene as an eluent to afford 378 mg of methyl α-methylthio-α-(6-methoxy-2-naphthyl)propionate in a yield of 86%.

NMR (CDCl$_3$): δ1.88 (s, 3H), 1.94 (s, 3H), 3.72 (s, 3H), 3.79 (s, 3H), 7.0–7.8 (m, 6H).

EXAMPLE 32

Methyl α-methylthio-α-(6-methoxy-2-naphthyl)propionate (372 mg) was dissolved in 2 ml of methanol, and 10 ml of a methanol suspension of 5.0 cc of Raney nickel (W-II) was added, and the mixture was stirred at room temperature for 15 hours. The insoluble matter was separated by filtration, and the filtrate was concentrated under reduced pressure. Methylene chloride was added to the residue. The insoluble matter was separated by filtration. The filtrate was concentrated under reduced pressure, and the residue was chromatograhed on a silica gel column using benzene as an eluent to afford 212 mg of methyl α-(6-methoxy-2-naphthyl)propionate as colorless crystals in a yield of 68%. The product had a melting point (from petroleum ether) of 67° to 69° C. The IR and NMR spectra of this product coincided with those of the authentic sample.

EXAMPLE 33

Methyl α-methylthio-[m-(α,α-dimethoxybenzyl)phenyl]acetate (444 mg) was dissolved in 4 ml of dimethyl sulfoxide, and 55 mg of sodium hydride (65% content) was added. The mixture was stirred at room temperature for 20 minutes. Methyl iodide (0.20 ml) was added dropwise over the course of 3 minutes, and the mixture was further stirred at room temperature for 30 minutes. An aqueous solution of ammonium chloride (200 mg/30 ml) was added, and the mixture was extracted three times with 20 ml of diethyl ether. The organic layer was washed three times with 10 ml of water, dried over anhydrous sodium sulfate, and the residue was chromatographed on a column of Florisil using benzene and methylene chloride as eluents to afford 386 mg of methyl α-methylthio-α-[m-(α,α-dimethoxybenzyl)phenyl]propionate as an oil in a yield of 84%.

IR (neat): 2820, 1730, 1240, 1095, 1055, 760, 705 cm$^{-1}$.

NMR (CDCl$_3$): δ1.73 (s, 3H), 1.86 (s, 3H), 3.07 (s, 6H), 3.66 (s, 3H), 7.1–7.6 (m, 9H).

Mass spectrum: m/e 360 (M+), 329, 313, 301, 283, 255 (base peak), 151, 135, 105.

EXAMPLE 34 (FORMULA II)

Methyl α-methylthio-α-[m-(α,α-dimethoxybenzyl)-phenyl]-propionate (211 mg) was dissolved in 1 ml of ethanol, and 5 ml of an ethanol suspension of 2 cc of Raney nickel (W-II) was added. The mixture was stirred at room temperature for 1 hour. The insoluble matter was separated by filtration, and washed with 40 ml of ethanol. The filtrate and the washing are combined and concentrated under reduced pressure, and 30 ml of methylene chloride was added to the residue. The insoluble matter was separated by filtration, and the solvent was evaporated off under reduced pressure to afford 159 mg of methyl α-[m-(α,α-dimethoxybenzyl)-phenyl]propionate as an oil in a yield of 86%.

IR (neat): 2825, 1745, 1165, 1095, 1060, 760, 710, 700 cm$^{-1}$.

NMR (CDCl$_3$): δ1.43 (d, 3H, J=7 Hz), 3.06 (s, 6H), 3.55 (s, 3H), 3.65 (q, 1H, J=7 Hz), 7.1–7.5 (m, 9H).

Mass spectrum: m/e 314 (M+), 283 (base peak), 255, 237, 151, 105.

EXAMPLE 35 (FORMULA II)

Methyl α-methylthio[m-(2-phenyl-1,3-dioxa-2-cyclopentyl)phenyl]acetate (6.88 g) was dissolved in 30 ml of anhydrous dimethyl sulfoxide. While cooling at 15° C., 810 mg (65% content) of sodium hydride was added, and the mixture was stirred for 1 hour. Hydrogen evolved gradually to form a reddish brown solution. While cooling at 15° C., 1.5 ml of methyl iodide was added to this solution, whereupon the color vanished immediately. After stirring for 5 minutes, an aqueous solution of ammonium chloride (2 g/10 ml) was added, and then 40 ml of water was added. The mixture was extracted first with 50 ml of diethyl ether, and then three times with 10 ml of diethyl ether. The extract was washed three times with 10 ml of water, dried over anhydrous sodium sulfate, and concentrated under reduced pressure. The residue was chromatographed on a column of Florisil using benzene and diethyl ether as eluents to afford 6.14 g of methyl α-methylthio-α-[m-(2-phenyl-1,3-dioxa-2-cyclopentyl)phenyl]propionate as a colorless oil in a yield of 86%.

An analytical sample was obtained by short-path distillation (bath temperature 180° C./0.01 mmHg) of this product.

IR (neat): 1730, 1240, 1175, 1090, 995, 710, 650 cm$^{-1}$.

NMR (CDCl$_3$): δ1.73 (s, 3H), 1.89 (s, 3H), 3.66 (s, 3H), 3.98 (s, 4H), 7.1–7.6 (m, 9H).

Elemental analysis for $C_{20}H_{22}O_4S$: Calculated: C, 67.01; H, 6.19; S, 8.95%. Found: C, 66.75; H, 6.24; S, 9.03%.

EXAMPLE 36 (FORMULA II)

Methyl α-methylthio[m-(5,5-dimethyl-2-phenyl-1,3-dioxa-2-cyclohexyl)phenyl]acetate (406 mg) was dissolved in 3 ml of anhydrous dimethyl sulfoxide. Sodium hydride (50 mg; 65% content) was added, and the mixture was stirred for 15 minutes at room temperature. The mixture turned into a reddish brown solution with the evolution of hydrogen. When 0.15 ml of methyl iodide was added to the solution, its color vanished. The mixture was stirred for an additional 10 minutes at room temperature. An aqueous solution of ammonium chloride (0.2 g/30 ml) was added, and the mixture was extracted three times with 20 ml of diethyl ether. The organic layer was washed twice with 10 ml of water, dried over anhydrous sodium sulfate, and concentrated under reduced pressure. The residue was chromatographed on a column of Florisil using benzene and diethyl ether as eluents to afford 368 mg of methyl α-methylthio-α-[m-(5,5-dimethyl-2-phenyl-1,3-dioxa-2-cyclohexyl)phenyl]propionate as a colorless oily substance in a yield of 87%.

IR (neat): 2860, 1730, 1245, 1100, 1025, 760, 710 cm$^{-1}$.

NMR (CDCl$_3$): δ0.95 (s, 6H), 1.86 (s, 3H), 1.93 (s, 3H), 3.60 (s, 4H), 3.72 (s, 3H), 7.2–7.7 (m, 9H).

Mass spectrum: m/e 400 (M+), 385, 353, 341, 323, 267, 255, 191, 105 (base peak).

EXAMPLE 37 (FORMULA II)

Methanol (10 ml) and 1 ml of water were added to 2.52 g of methyl α-methylthio-α-[m-(2phenyl-1,3-dioxa-2-cyclopentyl)phenyl]propionate, and 0.2 ml of conc.

hydrochloric acid was added. The mixture was heated for 20 minutes under reflux. After cooling, 20 ml of water was added, and the mixture was extracted with 50 ml and 10 ml respectively of methylene chloride. The extract was washed twice with 10 ml of water, and dried over anhydrous sodium sulfate. The solvent was evaporated under reduced pressure. The residue was chromatographed on a column of silica gel using methylene chloride as an eluent to afford 2.10 g of methyl α-methylthio-α-(m-benzoylphenyl)-propionate as a colorless oil in a yield of 95%.

An analytical sample was obtained by short-path distillation (bath temperature 170° to 180° C./0.01 mmHg) of the product.

$n_D^{25}$: 1.5934

IR (neat): 1730, 1660, 1600, 1450, 1320, 1285, 1245, 1210, 715, 700 645 cm$^{-1}$.

NMR (CDCl$_3$): δ1.84 (s, 3H), 2.02 (s, 3H), 3.79 (s, 3H), 7.4–8.0 (m, 9H).

Elemental analysis for $C_{18}H_{18}O_3S$: Calculated: C, 68.76; H, 5.77; S, 10.20%. Found: C, 68.57; H, 5.96; S, 10.01%.

EXAMPLE 38 (FORMULA II)

To 978 mg of methyl α-methylthio-α-[m-(α,α-dimethoxybenzyl)phenyl]propionate were added 2 ml of 1,2-dimethoxyethane and 0.5 ml of water, and 0.2 ml of conc. hydrochloric acid was further added. The mixture was stirred at room temperature for 15 hours. The reaction solution was diluted with 50 ml of methylene chloride, and dried over anhydrous sodium sulfate. The drying agent was separated by filtration, and the filtrate was concentrated under reduced pressure to afford 874 mg of methyl α-methylthio-α-(m-benzoylphenyl)propionate. The product was found to be substantially pure by its NMR and GLC.

EXAMPLE 39 (FORMULA II)

Methyl α-methylthio(m-benzoylphenyl)acetate (713 mg) was dissolved in 6 ml of anhydrous dimethylformamide, and with ice cooling, 100 mg (65% content) of sodium hydride was added. The mixture was stirred for 30 minutes. The reaction mixture turned black violet. When 0.3 ml of methyl iodide was added with ice cooling, the color vanished immediately. The mixture was stirred for 10 minutes at room temperature, and then an aqueous solution of ammonium chloride (500 mg/30 ml) was added. The mixture was extracted three times with 20 ml of diethyl ether. The organic layer was washed three times with 10 ml of water, dried over anhydrous sodium sulfate, and concentrated under reduced pressure. The residue was chromatographed on a silica gel column using benzene and methylene chloride as eluents to give 111 mg of methyl α-methylthio-α-(m-benzoylphenyl)propionate and 461 mg of a mixture which was shown by NMR analysis to consist of methyl α-methylthio(m-benzoylphenyl)acetate and methyl α-methylthio-α-(m-benzoylphenyl)propionate (the mole ratio=7:11).

From the above analysis, the yield of the methyl α-methylthio-α-(m-benzoylphenyl)propionate was calculated as 53%.

EXAMPLE 40

Methyl α-methylthio-α-(m-benzoylphenyl)propionate (314 mg) was dissolved in 1 ml of anhydrous methanol, and 1.0 ml (2.34 M) of a methanol solution of sodium salt of methyl mercaptan was added. The mixture was heated under reflux for 2.5 hours. To hydrolyze the resulting ester, 100 mg of sodium hydroxide and 0.5 ml of water were added, and the mixture was further heated under reflux for 30 minutes. The reaction mixture was diluted with 20 ml of water, and adjusted to pH 1 with conc. hydrochloric acid. The mixture was extracted three times with 30, 10 and 10 ml, respectively, of diethyl ether. The organic layer was washed with 10 ml of water, dried over anhydrous sodium sulfate, and concentrated under reduced pressure. The oily residue was chromatographed on a silica gel column using methylene chloride as an eluent to afford 224 mg of α-(benzoylphenyl)propionate acid as colorless crystals in a yield of 88%.

Melting point: 95°–96° C. (from n-hexane-diethyl ether)

IR (KBr): 3300–2500, 1700, 1655, 1290, 1230, 970, 715, 705, 690 cm$^{-1}$.

NMR (CDCl$_3$): δ1.52 (d, 3H, J=7 Hz), 3.77 (q, 1H, J=7 Hz), 7.3–7.8 (m, 9H), 11.60 (broad s, 1H).

Elemental analysis for $C_{16}H_{14}O_3$: Calculated: C, 75.57; H, 5.55%. Found: C, 75.53; H, 5.61%.

EXAMPLE 41

Methyl α-methylthio-α-(m-benzoylphenyl)propionate (628 mg) was dissolved in 2 ml of anhydrous methanol, and 1.5 ml (2.34 M) of a methanol solution of sodium salt of methyl mercaptan was added. The mixture was heated under reflux for 1.5 hours. After cooling, an aqueous solution of ammonium chloride (2.0 g/10 ml) was added to stop the reaction. The reaction mixture was diluted with 10 ml of water, and then extracted with 30 ml of diethyl ether and then twice with 10 ml of diethyl ether. The extract was washed with 20 ml of a saturated aqueous solution of sodium hydrogen carbonate and then with 5 ml of water, and dried over anhydrous sodium sulfate. The product was concentrated under reduced pressure, and the residue (377 mg) was chromatographed on a silica gel column using methylene chloride as an eluent to afford 363 mg of methyl α-(m-benzoylphenyl)propionate as a colorless oil in a yield of 68%.

An analytical sample was obtained by short-path distillation of this product (bath temperature 150°–160° C./0.01 mmHg).

IR (neat): 1740, 1660, 1600, 1450 1320, 1290, 1210, 1165, 720, 705, 645 cm$^{-1}$.

NMR (CDCl$_3$): δ1.51 (d, 3H, J=7 Hz), 3.66 (s, 3H), 3.78 (q, 1H, J=7 Hz), 7.3–7.9 (m, 9H).

Elemental analysis for $C_{17}H_{16}O_3$: Calculated: C, 76.10; H, 6.01%. Found: C, 75.93; H. 6.09%.

The washings were combined, adjusted to pH 1 with conc. hydrochloric acid, and extracted three times with 20 ml, 10 ml and 10 ml respectively of diethyl ether. The organic layer was washed with 10 ml of water, dried with anhydrous sodium sulfate, and concentrated under reduced pressure to afford 34 mg (7%) of α-(m-benzoylphenyl)propionic acid.

EXAMPLE 42

Methyl α-methylthio-α-(m-benzoylphenyl)propionate (221 mg) was dissolved in 2 ml of anhydrous methanol, and 0.20 ml of thiophenol and 0.20 ml (2.53 M) of a methanol solution of sodium methoxide were added. The mixture was heated under reflux for 48 hours. An aqueous solution of ammonium chloride (0.50 g/30 ml) was added, and the mixture was extracted twice with 20 ml of diethyl ether. The extract was dried over anhydrous sodium sulfate, and concentrated under reduced pressure. The residue was chromatographed on a silica gel column. The excess of thiophenol was eluted with benzene, and then the residue was eluted with methylene chloride to afford 112 mg of a colorless oily substance. From an NMR analysis, this product was determined to be a mixture of methyl α-(m-benzoylphenyl)propionate and methyl α-methylthio-α-(m-benzoylphenyl)propionate (the mole ratio=122:25). The yield of the methyl α-(m-benzoylphenyl)propionate was calculated as 48%.

EXAMPLE 43

To 456 mg of methyl α-methylthio-α-[m-(2-phenyl-1,3-dioxa-2-cyclopentyl)phenyl]propionate were added 2.00 g of potassium hydroxide and 10 ml of water. The mixture was heated under reflux with stirring. A mixture of 100 mg of zinc powder and 10 mg of copper sulfate pentahydrate was added three times at 30 minutes' intervals, and the mixture was further heated under reflux for 24 hours with stirring. After cooling, 20 ml of water was added. The insoluble matter was separated by filtration, and washed with 20 ml of water. The filtrate and the washing were combined, and extracted with 10 ml of diethyl ether. The organic layer was adjusted to pH 1 with 3.5 ml of conc. hydrochloric acid, and extracted four times with 20 ml of diethyl ether. The organic layer was washed with 10 ml of water, and concentrated under reduced pressure to afford α[m-(2-phenyl-1,3-dioxa-2-cyclopentyl)phenyl]propionic acid as colorless crystals.

Melting point: 91°–94° C.

IR (KBr): 3200–2800, 2890, 1710, 1285, 1225, 1210, 1085, 1075, 710 cm$^{-1}$.

NMR (CDCl$_3$): δ1.43 (d, 3H, J=7 Hz), 3.67 (q, 1H, J=7 Hz), 3.92 (s, 4H), 7.1–7.7 (m, 9H).

To the resulting product were added 3 ml of 1,2-dimethoxyethane, 1 ml of water and 0.2 ml of conc. hydrochloric acid, and the mixture was heated under reflux for 40 minutes. Diethyl ether (50 ml) was added, and the resulting mixture was washed three times with 5 ml of water, dried over anhydrous sodium sulfate, and concentrated under reduced pressure. The oily residue was chromatographed on a silica gel column using methylene chloride as an eluent to afford 276 mg of α-(m-benzoylphenyl)propionic acid in a yield of 85% as colorless crystals.

EXAMPLE 44

Water (4 ml) was added to a mixture consisting of 269 mg of methyl α-methylthio-α-[m-(α,α-dimethoxybenzyl)phenyl]propionate, 500 mg of zinc powder and 80 mg of copper sulfate pentahydrate. Then, 500 mg of potassium hydroxide (85%) was added, and the mixture was stirred at the refluxing temperature for 44 hours. Water (4 ml) was further added, and with stirring, the mixture was heated under reflux for 3 hours. After cooling, the insoluble matter was separated by filtration, and washed with 20 ml of water. The filtrate and the washing were combined and adjusted to pH 1 with 2.0 ml of conc. hydrochloric acid. The mixture was stirred at 60° C. for 40 minutes and then, extracted three times with 20 ml of diethyl ether. The extract was washed with 10 ml of water, and dried over anhydrous sodium sulfate, and concentrated under reduced pressure. The residue was chromatographed on a silica gel column using methylene chloride as an eluent to afford 162 mg of α-(m-benzoylphenyl)propionic acid in a yield of 85%.

EXAMPLE 45 (FORMULA II)

Methanol (4 ml) and 1 ml of water were added to 1.277 g of methyl α-methylthio-α-[m-(2-phenyl-1,3-dioxa-2-cyclopentyl)phenyl]propionate. Furthermore, 350 mg of sodium hydroxide was added, and the mixture was heated under reflux for 2 hours. After cooling, 30 ml of water was added, and the mixture was washed twice with 10 ml of diethyl ether. To the aqueous layer was added about 6 ml of 3.5% hydrochloric acid to adjust its pH to 3. It was then extracted four times with 20 ml of diethyl ether. The organic layer was washed twice with 10 ml of water, dried over anhydrous sodium sulfate, and evaporated under reduced pressure to afford 1.199 g of α-methylthio-α-[m-(2-phenyl-1,3-dioxa-2-cyclopentyl)phenyl]propionic acid as colorless crystals.

Melting point: 118°–120° C. (from n-hexane-carbon tetrachloride)

IR (KBr): 3300–2300, 1700, 1265, 1220, 1200, 1190, 1180, 720, 705 cm$^{-1}$.

NMR (CDCl$_3$): δ1.78 (s, 3H), 1.96 (s, 3H), 4.04 (s, 4H), 7.2–7.6 (m, 8H), 7.77 (broad s, 1H), 10.28 (broad s, 1H).

EXAMPLE 46

α-Methylthio-α-[m-(2-phenyl-1,3-dioxa-2-cyclopentyl) phenyl]propionic acid (682 mg) was dissolved in 8 ml of anhydrous tetrahydrofuran. Anhydrous t-butanol (2 ml) was added. Metallic sodium (210 mg) was added in three portions, and the mixture was stirred at room temperature for 15 minutes. When the mixture was heated under reflux for 1.5 hours, the metallic sodium was consumed completely. After cooling, 30 ml of water was added to the solution, and it was washed with 10 ml of diethyl ether. To the aqueous layer was added 8 ml of 3.5% hydrochloric acid to adjust its pH to 1. It was then extracted three times with 20 ml of diethyl ether. The organic layer was washed with 10 ml of water, dried over anhydrous sodium sulfate, and concentrated under reduced pressure to afford 622 mg of an oily substance. From its MNR spectrum, this product was determined to be a mixture (the mole ratio=3:7) of α-methylthio-α-[m-(2-phenyl-1,3-dioxa-2-cyclopentyl)phenyl]propionic acid and α-[m-(2-phenyl-1,3-dioxa-2-cyclopentyl phenyl]propionic acid.

EXAMPLE 47 (FORMULA II)

Methyl α-methylthio(2-thienyl)acetate (1.446 g) was dissolved in 8 ml of anhydrous dimethyl sulfoxide, and while cooling, at 20° C., 290 mg (65% content) of sodium hydride was added. When the mixture was stirred for 30 minutes, the reaction solution turned bluish violet. Methyl iodide (0.60 ml) was added to it over the course of 3 minutes, and the mixture was stirred at 20° C. for 1.5 hours, whereupon the bluish violet color gradually vanished. An aqueous solution of ammonium chloride (0.40 g/30 ml) was added, and the mixture was extracted three times with 20 ml of diethyl ether. The organic layer was washed three times with 10 ml of water, and dried over anhydrous sodium sulfate. After concentration under reduced pressure, the residue was chromatographed on a silica gel column using benzene as an eluent to afford 1.410 g of methyl α-methylthio-α-(2-thienyl)propionate in a yield of 91% as a colorless liquid.

Boiling point: 87°-88° C./0.3 mmHg

IR (neat): 1735, 1450, 1435, 1255, 1235, 1105, 705 cm$^{-1}$.

NMR (CDCl$_3$): δ1.89 (s, 3H), 2.01 (s, 3H), 3.71 (s, 3H), 6.7-7.3 (m, 3H).

Elemental analysis for C$_9$H$_{12}$O$_2$S$_2$: Calculated: C, 49.97; H, 5.59; S, 29.65%. Found: C, 50.06; H, 5.65; S, 29.81.

EXAMPLE 48 (FORMULA II)

Methyl α-methylthio(2-thienyl)acetate (1.980 g) was dissolved in 20 ml of anhydrous dimethylformamide, and with stirring at room temperature, 400 mg (65% content) of sodium hydride was added, whereupon hydrogen evolved vigorously. Ten minutes later, the reaction solution was cooled with ice, and 0.75 ml of methyl iodide was added over the course of 1 minute. The mixture was stirred at room temperature for 1 hour. An aqueous solution of ammonium chloride (0.50 g/30 ml) was added, and the mixture was extracted four times with 20 ml of diethyl ether. The organic layer was washed four times with 10 ml of water, dried over anhydrous sodium sulfate, and concentrated under reduced pressure. The residue was chromatographed on a silica gel column using benzene as an eluent to afford 1.949 g of methyl α-methylthio-α-(2-thienyl)propionate in a yield of 92%.

EXAMPLE 49 (FORMULA II)

Methanol (6 ml) and 4 ml of water were added to 1.08 g of methyl α-methylthio-α-(2-thienyl)propionate, and 500 mg of sodium hydroxide was added. The mixture was heated under reflux for 1 hour. Water (20 ml) was added, and the mixture was extracted with 10 ml of diethyl ether. The aqueous layer was adjusted to pH 1 with conc. hydrochloric acid, and extracted three times with 20 ml of diethyl ether. The organic layer was washed with 10 ml of water, and dried over anhydrous sodium sulfate. Evaporation of the solvent under reduced pressure afforded 1.00 g of α-methylthio-α-(2-thienyl)propionic acid as colorless crystals in a yield of 99%.

Melting point: 58° C. (from hexane-carbon tetrachloride)

IR (KBr): 3200-2400, 1700, 1280, 1245, 920, 700 cm$^{-1}$.

NMR (CDCl$_3$): δ1.91 (s, 3H), 2.06 (s, 3H), 6.8-7.3 (m, 3H), 12.0 (broad s, 1H).

Elemental analysis for C$_8$H$_{10}$O$_2$S$_2$: Calculated: C, 47.50; H, 4.98; S, 31.70%. Found: C, 47.51; H, 4.89; S, 31.48%.

EXAMPLE 50

Methyl α-methylthio-α-(2-thienyl)propionate (432 g) was dissolved in 4 ml of acetic acid, and 32 mg of anhydrous copper sulfate and 400 mg of zinc powder were added. With stirring, the mixture was heated under reflux for 3.5 hours. After cooling, 30 ml of diethyl ether was added, and the insoluble matter was separated by filtration, followed by washing with 10 ml of diethyl ether. The filtrate and the washing were combined, and washed with 10 ml of water. After 20 ml of water was further added, sodium carbonate was gradually added to neutralize the acetic acid present. The organic layer was then separated, washed with 10 ml of water, and dried over anhydrous sodium sulfate. The solvent was evaporated under reduced pressure, and the residue was subjected to short-path distillation (bath temperature 100°-110° C./8 mmHg) to afford 297 mg of methyl α-(2-thienyl)propionate as a colorless oil in a yield of 87%.

IR (neat): 1740, 1455, 1435, 1380, 1330, 1200, 1165, 1055, 855, 700 cm$^{-1}$

NMR (CDCl$_3$): δ1.59 (d, 3H, J=7 Hz), 3.70 (s, 3H), 4.01 (q, 1H, J=7 Hz), 6.9-7.0 (m, 2H), 7.1-7.3 (m, 1H)

Elemental analysis for C$_8$H$_{10}$O$_2$S: Calculated: C, 56.44; H, 5.92; S, 18.84%. Found: C, 56.26; H, 5.88; S, 18.74%.

EXAMPLE 51

Zinc powder (150 mg), 2 ml of conc. hydrochloric acid and 1 ml of water were added to 542 mg of α-methylthio-α-(2-thienyl)propionic acid, and the mixture was stirred at the refluxing temperature for 40 minutes. After cooling, it was extracted three times with 10 ml of diethyl ether. The organic layer was washed twice with 10 ml of water, and dried over anhydrous sodium sulfate. The solvent was evaporated under reduced pressure, and the residue was subjected to short-path distillation (bath temperature 140°-160° C./12 mmHg) to afford 245 mg of α-(2-thienyl)propionic acid in a yield of 58%.

IR (neat): 3500-2400, 1710, 1460, 1410, 1240, 700 cm$^{-1}$

NMR (CDCl$_3$) δ1.60 (d, 3H, J=7 Hz), 4.02 (q, 1H, J=7 Hz), 6.9-7.1 (m, 2H), 7.1-7.3 (m, 1H), 11.06 (broad s, 1H)

Elemental analysis for C$_{17}$H$_8$O$_2$S: Calculated: C, 53.82; H, 5.16; S, 20.53%. Found: C, 53.47; H, 5.19; S, 20.70%.

EXAMPLE 52 (FORMULA II)

Methyl α-methylthio[5-(α,α-dimethoxybenzyl)-2-thienyl]acetate (1.162 g) was dissolved in 6 ml of anhydrous dimethyl sulfoxide, and 150 mg (65% content) of sodium hydride was added. The mixture was stirred at room temperature for 30 minutes. Methyl iodide (0.30 ml) was added, and the mixture was stirred at room temperature for 15 minutes. An aqueous solution of ammonium chloride (0.5 g/30 ml) was added, and the mixture was extracted three times with 20 ml of diethyl ether. The extract was washed twice with 10 ml of water, dried over anhydrous magnesium sulfate, and concentrated under reduced pressure. The residue was chromatographed on a column of Florisil using benzene as an eluent to afford 932 mg of methyl α-methylthio-α-[5-(α,α-dimethoxybenzyl)-2-thienyl]propionate in a yield of 77% as colorless crystals.

Melting point: 61.5°-62.5° C. (from n-hexane)

IR (KBr): 2830, 1730, 1240, 1090, 1050, 990, 760, 705 cm$^{-1}$

NMR (CDCl$_3$): δ1.86 (s, 3H), 2.00 (s, 3H), 3.12 (s, 6H), 3.72 (s, 3H), 6.65 (d, 1H, J=4 Hz), 6.84 (d, 1H, J=7 Hz), 7.2-7.4 (m, 3H), 7.4-7.6 (m, 2H)

Elemental analysis for C$_{18}$H$_{22}$O$_4$S$_2$: Calculated: C, 58.99; H, 6.05; S, 17.50%. Found: C, 59.08; H, 6.00; S, 17.61%.

EXAMPLE 53 (FORMULA II)

Methanol (5 ml) and 1 ml of water were added to 887 mg of methyl α-methylthio-α-[5-(α,α-dimethoxybenzyl)-2-thienyl]propionate, and 0.2 ml of conc. hydrochloric acid was added. The mixture was heated under reflux for 1 hour. After cooling, the mixture was concentrated under reduced pressure. The residue was chromatographed on a silica gel column using benzene as an eluent to afford 754 mg of methyl α-methylthio-α-(5-benzoyl-2-thienyl)propionate as an oil in a yield of 97%.

IR (neat): 1735, 1635, 1450, 1290, 1250, 1105, 865, 715, 700 cm$^{-1}$

NMR (CDCl$_3$): δ1.92 (s, 3H), 2.07 (s, 3H), 3.76 (s, 3H), 7.11 (d, 1H, J=4 Hz), 7.4-7.6 (m, 4H), 7.7-7.9 (m, 2H)

Mass spectrum: m/e=320 (M+), 273 (base peak), 261, 213, 105, 77

EXAMPLE 54

Methyl α-methylthio-α-(5-benzoyl-2-thienyl)propionate (320 mg) was dissolved in 1 ml of anhydrous methanol, and 1.0 ml (2.34 M) of a methanol solution of sodium salt of methyl mercaptan was added. The mixture was heated under reflux for 1 hour. In order to hydrolyze the ester, 1 ml of water was added and the mixture was heated under reflux for an additional 2 hours. After cooling, 20 ml of water was added, and the mixture was washed twice with 15 ml of methylene chloride. The aqueous layer was acidified to a pH of 1 with conc. hydrochloric acid, and extracted three times with 15 ml of methylene chloride. The organic layer was washed with 10 ml of water, and dried over anhydrous sodium sulfate. The solvent was evaporated under reduced pressure to afford 176 mg of α-(5-benzoyl-2-thienyl)propionic acid in a yield of 68%.

EXAMPLE 55

Methyl α-methylthio[p-[dimethoxy(2-thienyl)methyl]phenyl]acetate (457 mg) was dissolved in 3 ml of anhydrous dimethyl sulfoxide, and 60 mg (65% content) of sodium hydride was added. The mixture was stirred at room temperature for 30 minutes. Then, 0.15 ml of methyl iodide was added, and the mixture was stirred at room temperature for 20 minutes. After adding an aqueous solution of ammonium chloride (0.5 g/30 ml), the mixture was extracted three times with 20 ml of methylene chloride. The extract was washed twice with 10 ml of water, dried over anhydrous magnesium sulfate, and concentrated under reduced pressure. The residue was chromatographed on a Florisil column using benzene as an eluent to give 443 mg of methyl α-methylthio-α-[p-[dimethoxy(2-thienyl)methyl]phenyl]propionate as a colorless oil in a yield of 93%.

IR (neat): 2825, 1730, 1245, 1205, 1180, 1090, 1055, 790, 705 cm$^{-1}$

NMR (CDCl$_3$): δ1.78 (s, 3H), 1.96 (s, 3H), 3.18 (s, 6H), 3.77 (s, 3H), 6.8-7.1 (m, 2H), 7.2-7.3 (m, 1H), 7.47 (A$_2$B$_2$q, 4H)

Mass spectrum: m/e 366 (M+), 335, 319, 307, 288, 261, 245, 185, 157 111 (base peak), 75

EXAMPLE 56

Methanol (4 ml), 1 ml of water, and 0.2 ml of conc. hydrochloric acid were added to 405 mg of methyl α-methylthio-α-[p-[dimethoxy(2-thienyl)methyl]phenyl]propionate, and the resulting mixture was heated under reflux for 30 minutes. After the mixture was cooled and shaken with 50 ml of methylene chloride, the organic layer was separated, dried over anhydrous magnesium sulfate, and concentrated under reduced pressure to afford 320 mg of methyl α-[p-(2-thienylcarbonyl)phenyl]propionate as a colorless oil in a yield of 90%.

IR (neat): 1735, 1640, 1420, 1300, 1245, 1100, 730 cm$^{-1}$

NMR (CDCl$_3$): δ1.84 (s, 3H), 2.03 (s, 3H), 3.82 (s, 3H), 7.1-7.3 (m, 2H), 7.5-8.0 (m, 5H)

Mass spectrum: m/e 320 (M+), 273, 261, 245, 111 (base peak)

EXAMPLE 57

Methyl α-methylthio-α-[p-(2-thienylcarbonyl)phenyl)]propionate (288 mg) was dissolved in 1 ml of anhydrous methanol, and 1.0 ml of a methanol solution (2.34 M) of sodium salt of methyl mercaptan was added. The mixture was stirred at room temperature for 1 hour and heated under reflux for 30 minutes. After cooling, an aqueous solution of ammonium chloride (1.5 g/20 ml) was added to the reaction mixture. The mixture was extracted with 20 ml of methylene chloride and twice with 10 ml of methylene chloride. The extract was washed with 20 ml of a saturated aqueous solution of sodium hydrogen carbonate and with 10 ml of water, dried over anhydrous magnesium sulfate, and concentrated under reduced pressure to afford 117 mg of methyl α-[p-(2-thienylcarbonyl)phenyl]propionate in a yield of 47%.

The aqueous layer and the washings were combined, acidified to pH 1 with conc. hydrochloric acid, and extracted three times with 15 ml of diethyl ether. The extract was washed with 10 ml of water, dried over magnesium sulfate, and concentrated under reduced pressure to give 120 mg of α-[p-(2-thienylcarbonyl)phenyl]propionic acid in a yield of 51%.

What we claim is:

1. Alpha-methylthio-α-[p-(2-thienylcarbonyl)phenyl]propionic acid and its ester of the formula

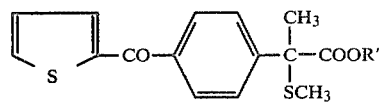

wherein R' represent H or C$_1$-C$_4$ alkyl.

* * * * *